United States Patent [19]

Steer

[11] Patent Number: 4,668,258
[45] Date of Patent: May 26, 1987

[54] GAS FILTER

[75] Inventor: Peter L. Steer, Reigate, England

[73] Assignee: Craig Medical Products Limited, Sussex, England

[21] Appl. No.: 819,575

[22] Filed: Jan. 17, 1986

[30] Foreign Application Priority Data

Feb. 14, 1985 [GB] United Kingdom ............... 8503749

[51] Int. Cl.⁴ .............................................. B01D 50/00
[52] U.S. Cl. .................................... 55/387; 55/385 C; 55/486; 55/524; 55/528; 55/DIG. 42; 604/333
[58] Field of Search ..................... 55/316, 385 C, 387, 55/486, 524, 528, DIG. 42; 604/333

[56] References Cited

U.S. PATENT DOCUMENTS

| | | | |
|---|---|---|---|
| 3,171,820 | 3/1965 | Volz | 55/528 X |
| 3,865,758 | 2/1975 | Yoshida et al. | 55/387 X |
| 4,046,939 | 9/1977 | Hart | 55/387 X |
| 4,268,286 | 5/1981 | Steer et al. | 55/387 X |
| 4,274,848 | 6/1981 | La Gro | 55/387 |
| 4,460,392 | 7/1984 | Poulsen et al. | 55/385 C |
| 4,479,818 | 10/1984 | Briggs et al. | 55/385 C |
| 4,490,145 | 12/1984 | Campbell | 604/333 |

FOREIGN PATENT DOCUMENTS

| | | | |
|---|---|---|---|
| 2804154 | 1/1979 | Fed. Rep. of Germany | 55/524 |
| 52-276 | 4/1977 | Japan | 55/387 |
| 2122090 | 8/1985 | United Kingdom . | |

Primary Examiner—Kathleen J. Prunner
Attorney, Agent, or Firm—Lawrence S. Levinson; Sanford J. Asman

[57] ABSTRACT

A gas filter suitable for an ostomy bag comprises a pad impregnated with a deodorizing agent (e.g., activated carbon) and made of any open cell plastic foam material which is laminated together with a first microporous membrane. A layer of water repellent material is applied on the surface of the first microporous membrane other than the surface to which the foam pad is attached. The layer is sufficiently thin so that gas flow through the microporous membrane is not blocked.

43 Claims, 4 Drawing Figures

U.S. Patent    May 26, 1987    4,668,258
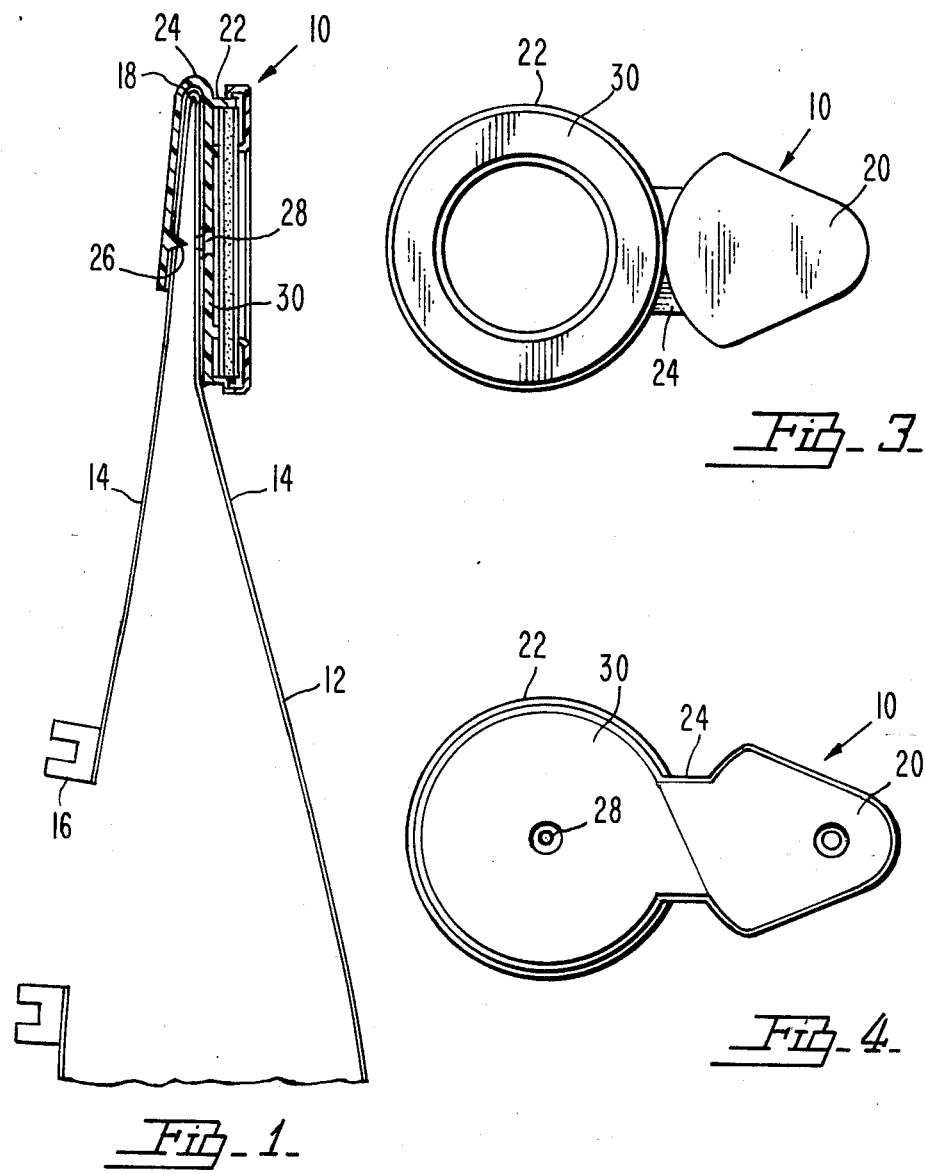
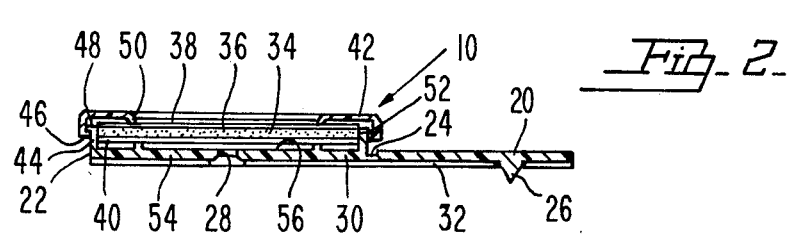

GAS FILTER

BACKGROUND OF THE INVENTION

The present invention relates to a gas filter. In particular, the invention relates to a gas filter primarily intended for use in or with an ostomy appliance.

An ostomy appliance, sometimes called an ostomy bag is a collection bag for receiving drainage from an abdominal opening following surgery, and an ostomy appliance is normally considered to comprise such a bag and means whereby it can be attached to a wearer.

Ostomy bags are well known, one example being shown in British Pat. No. 1,379,464. Since the discharge of the wearer of the bag often contains flatus gases, there have been continuing research and development efforts to devise a satisfactory way of allowing such gases to escape from the interior of the bag in such a way that they are filtered and deodorized. One design of a gas vent appliance or filter is illustrated in British Pat. No. 1,405,032. As shown in that patent, a deodorizing filter comprises a square filter pad comprised of matted fibres and granular activated carbon which may, if desired, be encapsulated in a film made of plastic or other suitable material.

Prior designs of gas filters for ostomy bags, which are sometimes also called ostomy pouches, of gas filters which can be attached to ostomy bags include gas filters which can be attached to bags which were not specially designed to have gas filters. An example is shown in U.S. Pat. No. 4,268,286 entitled ATTACHABLE FILTER AND OSTOMY BAG INCLUDING SAME which issued on May 19, 1981 to P. L. Steer, et al. Such prior designs did not yield a product which could be worn safely when swimming or when taking a shower. In other words, prior designs of ostomy bag filters were not waterproof to the extent desirable. In addition, previously known ostomy bag filters failed to allow passage of an adequate gas flow after being immersed in water.

Accordingly, a gas filter which could be attached to an ostomy bag which was not specially designed for such a filter and which would continue to operate, even after being wetted, would be desirable.

SUMMARY OF THE INVENTION

According to the present invention, a filter for an ostomy bag is comprised of a pad comprised of an open cell plastic foam which has been impregnated with a deodorizing agent. In accordance with the invention, the foam material is laminated with a first microporous membrane, with a layer of water repellent material on the surface of the membrane opposed to the surface to which the pad is attached. The layer of water repellent material is sufficiently thin that the pores in the membrane are not blocked against gas flow. The deodorizing agent is preferably activated carbon.

Also according to the invention, a filter carrier and a filter for ostomy use are provided. The filter includes a pad of reticulated polyurethane foam carrying particles of a deodorizing agent, and the filter carrier has a plastic housing which has a base wall having a hole formed therethrough which allows entry of gas to be deodorized and a retaining cap which is attached to the base wall so as to contain the foam pad within the housing. The peripheral wall is constructed to prevent the escape of any gas which exits from the edges of the pad. A water repellent coating is applied on at least the exposed surface of the pad within the peripheral wall.

BRIEF DESCRIPTION OF THE DRAWING

In the drawing:

FIG. 1 is a side view of the present invention mounted on an ostomy bag;

FIG. 2 is a cross-sectional view of the gas filter and the filter housing of FIG. 1;

FIG. 3 is a top view of the filter housing of FIG. 1 without the filter; and

FIG. 4 is a bottom view of the filter housing of FIG. 1.

DETAILED DESCRIPTION OF THE PREFERRED EMBODIMENT

Referring generally to FIG. 1, the present invention is a gas filter 10 which is intended for use in connection with an ostomy bag 12 of a type which is well known in the art. The ostomy bag 12 is typically comprised of a bag having plastic film walls 14 and a sealing connector 16 which is adapted to be attached to a mating connecter (not shown) which is adhesively attached to a wearer.

In use, the ostomy bag 12 collects material and gases. The purpose of the gas filter 10 of the present invention is to provide a means for venting gases from the ostomy bag 12 while deodorizing the gases which are vented. The gas filter 10 is adapted to be attached like a cuff link to an ostomy bag 12 which has not been specially adapted to receive a gas filter. Accordingly, the present invention provides a means for both attaching to the ostomy bag 12 and for providing a vent through the ostomy bag 12.

In accordance with the invention, the gas filter 10 attaches to the ostomy bag 12 by clipping over an edge 18 of the ostomy bag 12. A flap 20 on the gas filter 10 is attached to the filter housing 22 by means of a hinge 24. A spike 26 on the flap 20 is used to puncture a hole through both walls 14 of the ostomy bag 12. The spike 26 is aligned with an opening 28 on the base wall 30 of the filter housing 22. Accordingly, when the gas filter 10 is connected to the ostomy bag 12 the spike 26 serves to provide an opening through the ostomy bag 12 which is aligned with the opening 28 in the base wall 30 of the filter housing 22. The base wall 30 of the filter housing 22 and the surface of the flap 20 are each covered with an adhesive layer 32 whose purpose is to hold the gas filter 10 in place on the ostomy bag 12.

Referring now to FIGS. 2–4, the construction of the gas filter 10 is described. The gas filter 10 includes a filter housing 22, which is substantially cylindrical in the preferred embodiment of the invention. The filter housing 22 holds a filter 34 which is preferrably comprised of a foam pad 36 which is sandwiched between a first membrane 38 and a second membrane 40. The foam pad 36 is preferrably impregnated with a deodorizing agent, such as activated carbon which is used in the preferred embodiment of the invention. In the preferred embodiment, the foam pad 36 is made of polyurethane. However, any suitable, gas permeable material can be used. The membranes 38, 40 and the foam pad 36 may be secured together in any convenient way which integrates them into a single, unitary gas filter 34. By way of example, the membranes 38, 40 may be glued to the foam pad 36.

In the preferred embodiment 10 of the invention, the first membrane 38 is treated to make it water repellent.

The filter 34 is held in the housing 22 by means of a circular cap 42 which snaps onto the upper portion of the cylindrical wall 44 of the housing 22. The cap 42 includes a projection 46 which mates with a similar projection 48 on the upper surface of the wall 44. A lip 50 extends around the inner periphery of the cap 42. The lip 50 bears down upon the first membrane 38 thereby sealing the filter 34 in place within the housing 22 and insuring that any gases which enter the housing through the opening 28 must pass through the membrane 40, the foam pad 36, and the membrane 38. Accordingly, no gases can escape through the periphery 52 of the foam pad 36.

With continued reference to FIGS. 2-4, the central portion 54 of the base 30 of the housing 22 is somewhat thinner than the remainder of the base 30, thereby providing an air space 56 within the housing 22. The air space 56 surrounds the opening 28 in the the housing 22.

Gas entering through the opening 28 passes through the gas filter 34 and is deodorized by the deodorizing agent impregnated into the foam pad 36, activated charcoal in the preferred embodiment of the present invention.

The present invention is somewhat similar in overall mechanical design to the invention described in British Patent Application Ser. No. 2,122,090 which is entitled FOLD OVER FILTER FOR AN OSTOMY BAG. The filter housing 22 can be made by injection molding any one of a variety of plastics. A material called "Nylon 6" which is supplied by Imperial Chemical Industries, of Great Britain is presently preferred, but other materials, including polyethylene or polypropylene, may be used.

As will be understood by those skilled in the art, while the gas filter and housing illustrated are substantially circular, other shapes, e.g. oval, square, or rectangular could equally well be employed. In addition, while one valuable use for the gas filter of the present invention is as a filter for an ostomy appliance, the invention may be applied to other uses. It has a number of advantageous features, which include its ability to be applied to a bag which has not been specially fabricated for use with a gas filter.

The specific materials which are used to make the present invention are not critical to the invention, and other materials having the same, or similar, characteristics may be employed. In particular, the membranes 38, 40 are microporous membranes, made of polyurethane, but, alternatively, microporous layers of polyethylene, PVC or PTFE may be employed.

The membranes 38, 40 may be a 0.1-0.15 mm thick polyurethane foil with controlled microporous holes of predetermined size therein, obtained by adding preground soluble material (e.g. rock salt) to a solution of polyurethane which is then extrusion calendared to thickness and width. When formed it is passed through hot water baths to dissolve the salts, leaving minute holes in the plastic foam. The material known by the Trade Name PORVAIR may be used. Alternatively, the microporous membranes 38, 40 may be comprised of membranes of PTFE or FEP available from W. R. Gore of the United States.

A further alternative microporous membrane material is polyethylene or polyurethane or ethyl vinyl acetate (EVA) into which is mixed a controlled pore size of chalk (calcium carbonate). This is then extruded leaving the chalk in situ which, because of its porosity, allows air to flow therethrough. This membrane may be obtained from Messrs. Van Leer of Great Britain.

The foam pad 36 may be made of a polyurethane foam. In particular, it may be of a reticulated polyurethane foam having calibrated pores. For example, the foam know by the Trade Name BULPREN 7 may be used.

The foam pad should be made of a material which has the characteristics indicated in the following Table A:

TABLE A

| | |
|---|---|
| Density | 27–30 kg/m$^3$ |
| Compression Resistance | 3.4–4.6 KPA |
| Ultimate elongation | 350% |
| Tensile strength | 200 KPA |
| Tear strength | 6 N/cm |
| Porosity | 65–85 (PPI) |

The water repellent layer which is applied to the first membrane 38 may be applied to the membrane 38 either by spraying, by immersion, or by deposition. The water repellent layer may be comprised of polytetrafluorethylene (PTFE), fluorinated ethylene-propylene (FEP), silicone or wax. The coatings known by the Trade Names SCOTCHGUARD (3 ms) and ZEPEL may be used. The surface of the first membrane 38 to which the water repellent layer is applied may be pretreated to enhance the adhesion of the layer. Such pretreatment may be effected by a solvent, e.g., alcohol, ethyl, ethyl ketone, carbon tetrachloride, or acetone.

The pad may be made of an open cell polyurethane foam carrying substantially 200 grams of carbon per square meter (e.g., 180 to 220 g/m$^2$), and having an initial thickness of two millimeters, and a reduced thickness in the manufactured state of the filter of approximately 1 millimeter.

A satisfactory filter for ostomy bag use should have a gas permeability of at least about 8 ml per minutes per unit area at a pressure of 0.03 p.s.i. The reticulated foam polyurethane material referred to above (Table A) has a gas permeability of about 30 ml per minutes per unit area when dry. Prior known filters stated by their manufacturers to be suitable for ostomy bag use have broadly comparable gas permeabilities when dry but become obstructed or clogged when wet. That is, their gas permeability when wet (i.e. after immersion in water) is negligible or zero and hence they are unsatisfactory. Gas filters in accordance with the previous particular description, however, exhibit a gas permeability of approximately 10 ml per minute per unit area at 0.03 p.s.i. even after being submerged in water at depths of up to 30 inches for periods up to 30 minutes. Moreover, filters according to the particular description herein retain a fully adequate deodorizing capability even after submersion as described above. This conclusion as to retention of deodorizing capability is based on the results of tests using air containing substantially 20 parts per million of $H_2S$ fed through the filter at approximately 30 ml/min.

The reason why the described arrangement is so surprisingly effective after water immersion is not fully understood, but it is believed that the water repellent layer forms a thin boundary film over the material defining the walls of the microporous holes, as well as over the top surface of the membrane 38. It is believed that this thin film prevents or greatly inhibits the access of water to the particles of activated carbon or other deodorizing agent in the reticulated foam pad.

I claim:

1. A gas filter comprising a pad impregnated with a deodorizing agent and made of an open cell plastic foam material having a first surface and a second surface, said pad being laminated together with a first microporous membrane having a first surface and a second surface, said first surface of said foam material being laminated to said first surface of said microporous membrane, there being a layer of water repellent material on said second surface of said membrane, said layer of water repellent material being sufficiently thin that the pores in said microporous membrane are not blocked against gas flow, said first surface of said microporous membrane being pretreated with a solvent selected from the group consisting of alcohol, ethyl, ethyl ketone, carbon tetrachloride, and acetone whereby the adhesion of said water repellent layer will be enhanced.

2. The gas filter of claim 1 wherein said deodorizing agent is activated carbon.

3. The gas filter of claim 1 wherein the filter is comprised of a foam pad consisting of reticulated polyurethane foam carrying particles of a deodorizing agent.

4. The gas filter of claim 3 further comprising a filter housing for containing said gas filter, said filter housing being comprised of a plastic housing having a base wall with a hole formed therethrough for entry of gas to be deodorized and a peripheral wall of which traps said filter pad within said housing.

5. The gas filter of claim 1 in which said second surface of said pad is laminated to a second microporous membrane which is made of substantially the same material as said first microporous membrane.

6. The gas filter of claim 1 in which said water repellent layer is comprised of polytetrafluoroethylene (PTFE), fluorinated ethylene-propylene (FEP), silicone, or wax.

7. The gas filter of claim 1 in which the membrane is a 0.1–0.15 mm thick polyurethane foil with controlled microporous holes of predetermined size therein, obtained by adding preground soluble material (e.g., rock salt) to a solution of polyurethane which is then extrusion calendered to thickness and width and then passed through hot water baths to dissolve said soluble material, thereby leaving minute holes.

8. The gas filter of claim 1 in which said microporous membrane is selected from the group consisting of PTFE and FEP.

9. The gas filter of claim 1 in which said microporous membrane is polyethylene or polyurethane or ethyl vinyl acetate (EVA) into which is mixed a controlled pore size of chalk (calcium carbonate) which remains in situ and, being porous, allows gas to flow therethrough.

10. The gas filter of claim 1 in which said foam pad is of an open cell polyurethane foam carrying substantially 180 to 220 grams of carbon per square meter, and has a thickness in the manufactured state of the filter of approximately 1 millimeter.

11. The gas filter of claim 10 in which said second surface of said pad is laminated to a second microporous membrane which is substantially the same as said first microporous membrane.

12. The gas filter of claim 1 in which said pad is of reticulated polyurethane foam having the characteristics indicated in the following Table A:

TABLE A

| Density | 27–30 kg/m³ |
|---|---|
| Compression Resistance | 3.4–4.6 KPA |
| Ultimate elongation | 350% |
| Tensile strength | 200 KPA |
| Tear strength | 6 N/cm |
| Porosity | 65–85 (PPI) |

13. The gas filter of claim 12 in which said water repellent layer comprises a material selected from the group consisting of polytetrafluoroethylene (PTFE), fluorinated ethylene-propylene (FEP), silicone, and wax.

14. The gas filter of claim 13 in which said microporous membrane is a 0.1–0.15 mm thick polyurethane foil with controlled microporous holes of predetermined size therein, obtained by adding preground soluble material (e.g., rock salt) to a solution of polyurethane which is then extrusion calendered to thickness and width, then passed through hot water baths to dissolve the soluble material, thereby leaving minute holes.

15. A gas filter comprising a pad impregnated with a deodorizing agent and made of an open cell plastic foam material having a first surface and a second surface, said pad being laminated together with a first microporous membrane having a first surface and a second surface, said first surface of said foam material being laminated to said first surface of said microporous membrane, there being a layer of water repellent material on said second surface of said membrane, said layer of water repellent material being sufficiently thin that the pores in said microporous membrane are not blocked against gas flow, said microporous membrane being a 0.1–0.15 mm thick polyurethane foil with controlled microporous holes of predetermined size therein, obtained by adding preground soluble material (e.g., rock salt) to a solution of polyurethane which is then extrusion calendered to thickness and width and then passed through hot water baths to dissolve said soluble material, thereby leaving minute holes.

16. The gas filter of claim 15 wherein said deodorizing agent is activated carbon.

17. The gas filter of claim 15 wherein the filter is comprised of a foam pad consisting of reticulated polyurethane foam carrying particles of a deodorizing agent.

18. The gas filter of claim 17 further comprising a filter housing for containing said gas filter, said filter housing being comprised of a plastic housing having a base wall with a hole formed therethrough for entry of gas to be deodorized and a peripheral wall of which traps said filter pad within said housing.

19. The gas filter of claim 15 in which said second surface of said pad is laminated to a second microporous membrane which is made of substantially the same material as said first microporous membrane.

20. The gas filter of claim 15 in which said water repellent layer is comprised of polytetrafluoroethylene (PTFE), fluorinated ethylene-propylene (FEP), silicone, or wax.

21. The gas filter of claim 15 in which said foam pad is of an open cell polyurethane foam carrying substantially 180 to 220 grams of carbon per square meter, and has a thickness in the manufactured state of the filter of approximately 1 millimeter.

22. The gas filter of claim 15 in which said pad is of reticulated polyurethane foam having the characteristics indicated in the following Table A:

TABLE A

| Density | 27–30 kg/m³ |
|---|---|

TABLE A-continued

| | |
|---|---|
| Compression Resistance | 3.4–4.6 KPA |
| Ultimate elongation | 350% |
| Tensile strength | 200 KPA |
| Tear strength | 6 N/cm |
| Porosity | 65–85 (PPI) |

23. The gas filter of claim 22 in which said water repellent layer comprises a material selected from the group consisting of polytetrafluoroethylene (PTFE), fluorinated ethylene-propylene (FEP), silicone, and wax.

24. The gas filter of claim 23 in which said second surface of said microporous membrane, to which the water repellent layer is applied, is pretreated by a solvent selected from the group consisting of alcohol, ethyl, ethyl ketone, carbon tetrachloride, and acetone, whereby the adhesion of the layer will be enhanced.

25. A gas filter comprising a pad impregnated with a deodorizing agent and made of an open cell plastic foam material having a first surface and a second surface, said pad being laminated together with a first microporous membrane having a first surface and a second surface, said first surface of said foam material being laminated to said first surface of said microporous membrane, there being a layer of water repellent material on said second surface of said membrane, said layer of water repellent material being sufficiently thin that the pores in said microporous membrane are not blocked against gas flow, said microporous membrane consisting of polyethylene, polyurethane, or ethyl vinyl acetate (EVA) into which is mixed a controlled pore size of chalk (calcium carbonate) which remains in situ and, being porous, allows gas to flow therethrough.

26. The gas filter of claim 25 wherein said deodorizing agent is activated carbon.

27. The gas filter of claim 25 wherein the filter is comprised of a foam pad consisting of reticulated polyurethane foam carrying particles of a deodorizing agent.

28. The gas filter of claim 27 further comprising a filter housing for containing said gas filter, said filter housing being comprised of a plastic housing having a base wall with a hole formed therethrough for entry of gas to be deodorized and a peripheral wall of which traps said filter pad within said housing.

29. The gas filter of claim 25 in which said second surface of said pad is laminated to a second microporous membrane which is made of substantially the same material as said first microporous membrane.

30. The gas filter of claim 25 in which said water repellent layer is comprised of polytetrafluoroethylene (PTFE), fluorinated ethylene-propylene (FEP), silicone, or wax.

31. The gas filter of claim 25 in which said second surface of said microporous membrane is pretreated with a solvent selected from the group consisting of alcohol, ethyl, ethyl ketone, carbon tetrachloride, and acetone whereby the adhesion of said water repellent layer will be enhanced.

32. The gas filter of claim 25 in which said foam pad is of an open cell polyurethane foam carrying substantially 180 to 220 grams of carbon per square meter, and has a thickness in the manufactured state of the filter of approximately 1 millimeter.

33. The gas filter of claim 25 in which said pad is of reticulated polyurethane foam having the characteristics indicated in the following Table A:

TABLE A

| | |
|---|---|
| Density | 27–30 kg/m$^3$ |
| Compression Resistance | 3.4–4.6 KPA |
| Ultimate elongation | 350% |
| Tensile strength | 200 KPA |
| Tear strength | 6 N/cm |
| Porosity | 65–85 (PPI) |

34. The gas filter of claim 33 in which said water repellent layer comprises a material selected from the group consisting of polytetrafluoroethylene (PTFE), fluorinated ethylene-propylene (FEP), silicone, and wax.

35. The gas filter of claim 34 in which said second surface of said microporous membrane, to which the water repellent layer is applied, is pretreated by a solvent selected from the group consisting of alcohol, ethyl, ethyl ketone, carbon tetrachloride, and acetone, whereby the adhesion of the layer will be enhanced.

36. A gas filter comprising a pad impregnated with a deodorizing agent and made of an open cell plastic foam material having a first surface and a second surface, said pad being laminated together with a first microporous membrane having a first surface and a second surface, said first surface of said foam material being laminated to said first surface of said microporous membrane, there being a layer of water repellent material on said second surface of said membrane, said layer of water repellent material being sufficiently thin that the pores in said microporous membrane are not blocked against gas flow, said pad being comprised of reticulated polyurethane foam having the characteristics indicated in the following Table A:

TABLE A

| | |
|---|---|
| Density | 27–30 kg/m$^3$ |
| Compression Resistance | 3.4–4.6 KPA |
| Ultimate elongation | 350% |
| Tensile strength | 200 KPA |
| Tear strength | 6 N/cm |
| Porosity | 65–85 (PPI) | said water repellent layer comprising a material selected from the group consisting of polytetrafluoroethylene (PTFE), fluorinated ethylene-propylene (FEP), silicone, and wax, and said second surface of said microporous membrane, to which said water repellent layer is applied, is pretreated by a solvent selected from the group consisting of alcohol, ethyl, ethyl ketone, carbon tetrachloride, and acetone, whereby the adhesion of the layer will be enhanced.

37. The gas filter of claim 36 wherein said deodorizing agent is activated carbon.

38. The gas filter of claim 36 further comprising a filter housing for containing said gas filter, said filter housing being comprised of a plastic housing having a base wall with a hole formed therethrough for entry of gas to be deodorized and a peripheral wall of which traps said filter pad within said housing.

39. The gas filter of claim 36 in which said second surface of said pad is laminated to a second microporous membrane which is made of substantially the same material as said first microporous membrane.

40. The gas filter of claim 36 in which the membrane is a 0.1–0.15 mm thick polyurethane foil with controlled microporous holes of predetermined size therein, obtained by adding preground soluble material (e.g., rock salt) to a solution of polyurethane which is then extrusion calendered to thickness and width and then passed through hot water baths to dissolve said soluble material, thereby leaving minute holes.

41. The gas filter of claim 36 in which said microporous membrane is selected from the group consisting of PTFE and FEP.

42. The gas filter of claim 36 in which said microporous membrane is polyethylene or polyurethane or ethyl vinyl acetate (EVA) into which is mixed a controlled pore size of chalk (calcium carbonate) which remains in situ and, being porous, allows gas to flow therethrough.

43. The gas filter of claim 36 in which said foam pad carries substantially 180 to 220 grams of carbon per square meter, and has a thickness in the manufactured state of the filter of approximately 1 millimeter.

* * * * *